United States Patent
Wagner et al.

(10) Patent No.: US 9,541,433 B2
(45) Date of Patent: Jan. 10, 2017

(54) SENSOR DEVICE FOR DETECTING AT LEAST THE MOISTURE OF A FLOWING FLUID MEDIUM

(71) Applicant: Robert Bosch GmbH, Stuttgart (DE)

(72) Inventors: Ulrich Wagner, Munich (DE); Frank Steuber, Kornwestheim (DE); Uwe Konzelmann, Asperg (DE); Andreas Kaufmann, Sontheim An der Brenz (DE)

(73) Assignee: Robert Bosch GmbH, Stuttgart (DE)

( * ) Notice: Subject to any disclaimer, the term of this patent is extended or adjusted under 35 U.S.C. 154(b) by 185 days.

(21) Appl. No.: 14/366,652

(22) PCT Filed: Oct. 23, 2012

(86) PCT No.: PCT/EP2012/070927
§ 371 (c)(1),
(2) Date: Jun. 18, 2014

(87) PCT Pub. No.: WO2013/091940
PCT Pub. Date: Jun. 27, 2013

(65) Prior Publication Data
US 2015/0177037 A1    Jun. 25, 2015

(30) Foreign Application Priority Data

Dec. 21, 2011 (DE) .................. 10 2011 089 480

(51) Int. Cl.
*G01N 27/00* (2006.01)
*F02D 41/18* (2006.01)
(Continued)

(52) U.S. Cl.
CPC .............. *G01F 1/684* (2013.01); *F02M 26/46* (2016.02); *G01F 1/6842* (2013.01); *G01F 15/00* (2013.01);
(Continued)

(58) Field of Classification Search
CPC ...... G01N 27/00; G01N 27/02; G01N 27/048; G01N 27/223; F02D 35/00; F02D 45/00; F02D 2200/0418; F02M 26/46; Y10T 10/121

See application file for complete search history.

(56) References Cited

U.S. PATENT DOCUMENTS

2004/0007049 A1* 1/2004 Hoppach .................. G01K 7/16
73/29.02
2011/0226052 A1 9/2011 Speldrich et al.

FOREIGN PATENT DOCUMENTS

CN 101978264 A 2/2011
DE 35 11 509 10/1986
(Continued)

OTHER PUBLICATIONS

International Search Report for PCT/EP2012/070927, dated Jan. 7, 2013.
(Continued)

*Primary Examiner* — Nguyen Ha
(74) *Attorney, Agent, or Firm* — Norton Rose Fulbright US LLP; Gerard Messina (57) ABSTRACT

A sensor device for detecting at least one property of a flowing fluid medium includes: at least one moisture sensor; and at least one application device for applying the flowing fluid medium to the moisture sensor. The application device includes at least one diaphragm and at least one protective device which has at least one guide rib structure.

9 Claims, 2 Drawing Sheets (51) Int. Cl.
*G01F 1/684* (2006.01)
*G01F 15/00* (2006.01)
*G01N 27/04* (2006.01)
*G01N 27/22* (2006.01)
*G01F 15/14* (2006.01)

(52) U.S. Cl.
CPC ............ *G01F 15/14* (2013.01); *G01N 27/048* (2013.01); *G01N 27/223* (2013.01); *F02D 41/187* (2013.01); *F02D 2200/0418* (2013.01); *Y02T 10/121* (2013.01)

(56) References Cited

FOREIGN PATENT DOCUMENTS

| | | |
|---|---|---|
| DE | 10 2010 043 083 | 5/2012 |
| EP | 1 017 931 | 7/2000 |
| EP | 2 320 200 | 5/2011 |
| JP | 07239988 A * | 9/1995 ............ G01N 27/00 |

OTHER PUBLICATIONS

Robert Bosch GmbH: Sensoren im Kraftfahrzeug [Automotive Sensors], 2010 Edition, pp. 98-101; 2010 Edition, pp. 102-111,; 2010 Edition, pp. 146-148.

* cited by examiner

SENSOR DEVICE FOR DETECTING AT LEAST THE MOISTURE OF A FLOWING FLUID MEDIUM

BACKGROUND OF THE INVENTION

1. Field of the Invention

The present invention relates to a sensor device for detecting moisture of a flowing fluid medium.

2. Description of the Related Art

Numerous sensor devices for detecting at least one property of a flowing fluid medium are known from the related art. The property may basically be any arbitrary physically and/or chemically measurable property which may qualify and/or quantify a flowing fluid medium. In particular, the property may be moisture, in particular humidity, and/or a mass flow and/or a flow velocity and/or a volume flow and/or a pressure, for example an air pressure. The present invention is described below in particular with reference to gas sensors and concentration sensors as described, for example, in Robert Bosch GmbH: Sensoren im Kraftfahrzeug [Automotive Sensors], 2010 Edition, pages 98-101, and/or temperature sensors as described, for example, in Robert Bosch GmbH: Sensoren im Kraftfahrzeug, 2010 Edition, pages 102-111, and/or hot film air mass meters as described, for example, in Robert Bosch GmbH: Sensoren im Kraftfahrzeug, 2010 Edition, pages 146-148. The flowing fluid medium may be a gas or a liquid, for example. The present invention is described below with reference in particular to combustion air and/or exhaust gases of internal combustion engines, for example motor vehicles. However, other applications are also possible in principle.

For example, for more accurate pilot control of an injection quantity and/or for more precise control of exhaust gas recirculation (EGR), it may be necessary to detect the moisture, for example a specific moisture, of drawn-in combustion air. For example, moisture sensors are known from the related art which may be integrated into an air mass meter, or which as a separate sensor may be independently integrated into an intake tract.

Further applications of a sensor device, in particular a moisture sensor, are possible in principle. For example, in low-pressure exhaust gas recirculation (LP-EGR), water vapor may condense in an EGR cooler and/or in a charge air cooler. In particular there may be a risk of corrosion, for example due to acid formation, and/or water impact and/or freezing. In such a system, in each case a bypass is generally provided for an affected cooler, in particular for a charge air cooler, whereby the bypass may be controlled as a function of, among other things, the moisture content, for example the humidity, of the intake air, for example to avoid condensation in a targeted manner.

Capacitive moisture sensors in particular are known from the related art, in which the measuring effect may typically occur due to a change in the electrical capacitance of a hygroscopic polymer. In the process, water molecules typically diffuse into a dielectric as a function of the relative humidity, in particular a relative ambient humidity, and change a capacitance, in particular the electrical capacitance, of the polymer layer due to the high permittivity of water ($\varepsilon_w = 80$).

German patent application document DE 10 2010 043 083.3 proposes, for example, a sensor device for detecting a flow property of a fluid medium, the sensor device including at least one sensor housing within which at least one pressure sensor and at least one moisture sensor are accommodated. The sensor device may include at least one diaphragm, in particular at least one diaphragm that is at least partially permeable to moisture.

Moisture sensors may be designed as independent sensors or integrated into an air mass sensor. The sensor may include, for example, at least one electronic module and at least one sensor element that is fitted onto at least one plastic frame which has at least one diaphragm that is permeable to water vapor. In addition, the sensor may include at least one fitted-on electronics compartment cover having at least one recess which may allow, for example, a media exchange, in particular an exchange of the flowing fluid medium, with the air in the intake tract.

A sensor for an internal combustion engine, including an air mass meter which has a sensor element for detecting the drawn-in air mass, is known from published European patent document EP 1 017 931 B1. A moisture sensor and a pressure sensor as well as an evaluation circuit for processing the data which are output by the air mass meter or its sensor element, the moisture sensor, and the pressure sensor are provided adjacent to the air mass meter or its sensor element, and situated in a single housing.

The sensor devices known from the related art have several disadvantages. For example, an improvement in the robustness of the sensor device, which in particular includes a moisture sensor, against particle discharge from the flowing fluid medium, in particular a gaseous medium, to be measured would be desirable. Distortion of a measuring signal and/or destruction of the sensor device, for example the sensor, in particular by dust and/or air particles and/or oil and/or water droplets should be avoided. It would be desirable, for example, to protect the moisture sensor, in particular a hygroscopic film which encloses the moisture sensor, from the influence of foreign gases and/or condensation with dirty condensate. This could result in a reversible or irreversible change in a characteristic and/or an ohmic shunt and/or formation of a microclimate and/or corrosion of terminal contacts. Effective protection of the sensor device, in particular the sensor element, may be ensured, for example, by the diaphragm which is permeable to water vapor. For example, water droplets and/or dirty condensate and/or coarse dirt particles may thus be kept away from the sensor device, in particular the sensor element. However, due to solid particles that are entrained in the flowing fluid medium, in particular in the flow, the diaphragm itself may be mechanically damaged and/or filled with dirty condensate in such a way that, for example, water vapor may be hindered or prevented from passing through. In the worst case, a measuring effect may be completely lost, for example due to complete coverage of the surface of the diaphragm with an oil layer. Therefore, a sensor device for detecting at least one property of a flowing fluid medium would be desirable which at least partially suppresses or mitigates the disadvantages of the sensor devices known from the related art.

BRIEF SUMMARY OF THE INVENTION

Accordingly, a sensor device for detecting at least one property of a flowing fluid medium is provided. The sensor device may basically be understood as a device that is designed for detecting the at least one property of the flowing fluid medium. With regard to the at least one property to be detected, which may be detected qualitatively and/or quantitatively, reference may be made, for example, to the above description of the related art. In particular, the property may be at least a mass flow and/or at least a temperature and/or at least a fraction of a component and/or at least a humidity of the flowing fluid medium. The flowing fluid medium may in particular be a gas, preferably air. The sensor device is usable in particular in automotive engineering, for example in the intake tract and/or in the exhaust tract of an internal combustion engine. However, other fields of application are also possible in principle.

The sensor device includes at least one moisture sensor. The moisture sensor may basically be any arbitrary device that is configured to detect moisture. The detection of the moisture may be a qualitative and/or quantitative detection. For example, the moisture sensor may be configured to detect the presence of water in the flowing fluid medium, for example the humidity, in particular a relative humidity. The humidity may be a fraction of water vapor in a unit volume of the flowing fluid medium, whereby the humidity may be expressed in $g/m^3$, for example. The relative humidity may be understood to mean, for example, a quotient of the quantity of water vapor that is present in the flowing fluid medium at a certain temperature and the saturation quantity of water vapor that is possible at the same temperature, expressed as percent of relative humidity, for example. The moisture sensor may include, for example, at least one resistive and/or capacitive sensor element as known from the related art, for example.

For example, the moisture sensor may have at least one hygroscopic layer, the hygroscopic layer being able to reversibly store water as a function of the moisture, in particular the relative humidity. It is thus usually possible to effect a preferably drastic change in an electrical resistance and/or a planar capacitance, which may be evaluated for detecting the moisture. In capacitive moisture sensors, in particular moisture sensors, a hygroscopic, preferably insulating, layer, for example $Al_2O_3$ and/or a polymeric plastic, may usually be used as the dielectric of a capacitor. The hygroscopic layer may also be used at the same time as a carrier plate. The moisture sensor, in particular its capacitor, may include at least one electrode that is permeable to water vapor. Alternatively or additionally, the electrodes of the capacitor may have a comb-shaped structure. With increasing moisture, in particular with increasing relative humidity, the dielectric usually absorbs moisture, in particular water, whereby the capacitance of the sensor may preferably increase greatly. For example, the moisture sensor may also be designed as a resistive sensor. A resistive sensor may, for example, have at least one insulating substrate, in particular a hygroscopic substrate, for example a salt (LiCl) in a binder, in particular as a paste, between at least one electrode pair. The conductivity of this layer may change greatly with the moisture, in particular the relative humidity. This may be utilized for detecting the moisture. Examples of moisture sensors known from the related art are described in particular in Robert Bosch GmbH: Sensoren im Kraftfahrzeug, 2010 Edition, pages 98-101. However, in principle, other types of moisture sensors may alternatively or additionally be considered for use within the scope of the present invention.

The sensor device includes at least one application device for applying flowing fluid medium to the moisture sensor. The application device may basically be any arbitrary device that is configured to apply flowing fluid medium to the moisture sensor. The application device may, for example, be a connection between a main flow of the flowing fluid medium and the moisture sensor. For example, the application device may also be a supply line for supplying at least a portion of the flowing fluid medium to the moisture sensor. The application device may, for example, also include a discharge line for discharging the flowing fluid medium from the moisture sensor, or may be at least partially connected to a discharge line.

The application device may include, for example, at least one tube and/or at least one opening and/or at least one valve and/or at least one filter and/or at least one diffusion element and/or at least one cavity. The action may basically be understood to mean bringing at least a portion of the moisture sensor into contact with at least a portion of the flowing fluid medium, in particular in such a way that the moisture sensor may detect the moisture, in particular the relative humidity, of the flowing fluid medium.

The application device includes at least one diaphragm. The diaphragm may be understood, for example, as a separating layer that is configured to at least partially close at least a portion of the application device. For example, the diaphragm may be a diaphragm, in particular a semipermeable diaphragm, which is at least partially permeable to moisture. The diaphragm may preferably be configured to protect at least a fraction of the flowing fluid medium prior to contact with the moisture sensor and/or with at least one other sensor element and/or with at least one other portion of the sensor device. The diaphragm may preferably be configured to pass moisture, in particular humidity, through in particular to the moisture sensor in such a way that moisture, in particular humidity, for example relative humidity, may be detected in the most precise and/or reliable manner possible. The diaphragm may in particular be configured to keep dirt particles, for example oil particles and/or dust particles, away from the moisture sensor. The diaphragm may particularly preferably be a diaphragm that is at least partially permeable to moisture.

The application device also includes at least one protective device. The protective device may basically be any arbitrary device that is configured to protect the sensor device, in particular the moisture sensor or at least one additional sensor and/or at least one additional sensor element. The protective device may in particular be configured to protect the moisture sensor or at least one additional sensor element, preferably the diaphragm, from dirt particles or other environmental influences. The other environmental influences may, for example, be a high speed of the flowing fluid medium and/or a high temperature of the flowing fluid medium and/or a high pressure of the flowing fluid medium and/or a low pressure of the flowing fluid medium.

The protective device has at least one guide rib structure. The guide rib structure may basically be any arbitrary element that is configured to change at least one property of the flowing fluid medium, for example a speed of the flowing fluid medium and/or a flow of the flowing fluid medium and/or a flow direction of the flowing fluid medium and/or a vortex formation in the flowing fluid medium and/or a pressure of the flowing fluid medium and/or a temperature of the flowing fluid medium and/or at least one chemical property of the flowing fluid medium, for example a composition of the flowing fluid medium.

The sensor device may also include at least one flow sensor. The flow sensor may basically be understood to mean any arbitrary sensor element that is designed for detecting at least one flow property. The flow property may preferably be at least one mass flow of the flowing fluid medium. In particular, the flow sensor may be at least one hot film air mass meter (HFM), for example a hot film air mass meter chip. The flow sensor may, for example, be a hot film air mass meter as described in Robert Bosch GmbH: Sensoren im Kraftfahrzeug, 2010 Edition, pages 146-148. The flow sensor may include, for example, at least one channel, in particular a channel through which at least a portion of the flowing fluid medium may flow. The flow sensor may, for example, have at least one sensor housing, in particular a sensor housing which encloses the channel. The flow sensor may be designed as a plug-in sensor, for example. The flow sensor may include at least one sensor element. The sensor element may be accommodated in the channel, for example. The sensor element may be designed as a sensor chip on a sensor support, for example. The sensor chip may, for example, have at least one measuring surface, in particular a measuring surface over which at least a portion of the flowing fluid medium may flow. The flow sensor may include at least one hot film air mass meter, for example. The hot film air mass meter may in particular include at least one silicon chip, for example having at least one measuring surface over which the flowing fluid medium may flow. The flow sensor may have at least one heating element. The flow sensor may have at least one upstream temperature sensor and at least one downstream temperature sensor. At least one heating element and at least two temperature sensors, in particular an upstream temperature sensor and a downstream temperature sensor, may preferably be situated on the measuring surface, for example the sensor surface. The at least one flow property may be deduced from an asymmetry of a temperature profile that is measured with the aid of the temperature sensors. The at least one flow sensor may be situated, for example, on at least one sensor support of at least one electronic module. The sensor support may, for example, protrude at least partially into the flowing fluid medium. The electronic module may have a one-part design, for example. The electronic module may, for example, include in particular at least one control circuit and/or at least one evaluation circuit which may be configured to control the flow sensor and/or to receive signals of the flow sensor. The electronic module may have at least one circuit carrier, for example. The electronic module may also include in particular the at least one sensor support, which may preferably be mechanically connected to the circuit carrier. For example, the circuit carrier may be situated in an electronics compartment of a sensor housing. For example, the electronics compartment may be at least partially enclosed by the housing and/or by the diaphragm. The sensor housing and/or the electronics compartment may have at least one electronics compartment cover, in particular in order to reversibly or irreversibly at least partially close the electronics compartment. The sensor support may preferably protrude from the electronics compartment into the flowing fluid medium. It is particularly preferred for the sensor housing to have at least one channel through which flowing fluid medium may flow. The sensor support of the electronic module, which supports the flow sensor, for example, may protrude from the electronics compartment into the at least one channel in the sensor housing through which flowing fluid medium may flow. This at least one channel may in particular have a one-part design, but may also have at least one main channel and at least one bypass channel that branches off from this main channel, the sensor support preferably protruding into the bypass channel, as is known from the related art, for example. The circuit carrier of the electronic module may include in particular at least one printed circuit board, which may be used alone, for example, or which, for example, may also be mounted on a mechanical carrier, for example at least one stamped/bent part made of a metallic material, for example. The sensor support may be directly connected to the circuit carrier, or may also be connected to the carrier part, for example the stamped/bent part. Other configurations are also possible. It is thus conceivable, for example, for the electronic module to be made from at least one printed circuit board material, it being possible for the circuit carrier as well as the sensor support to be made from the printed circuit board material, preferably from a single piece of the printed circuit board material. Alternatively or additionally, it is also possible to use injection-molded printed circuit boards known from the related art as an electronic module. Various designs are conceivable in principle.

The sensor device may also include at least one temperature sensor. The temperature sensor may basically be any arbitrary sensor element that is configured to detect at least one temperature, preferably at least one temperature of the flowing fluid medium. The temperature sensor may, for example, be a temperature sensor known from the related art as described, for example, in Robert Bosch GmbH: Sensoren im Kraftfahrzeug, 2010 Edition, pages 102-111. The temperature sensor may be designed, for example, as a resistive sensor which includes at least one temperature-dependent electrical resistor, and/or as a negative temperature coefficient (NTC) thermistor, and/or as a thermoelement and/or as a thermometer.

The sensor device may also include at least one additional sensor element, for example at least one pressure sensor, for example for detecting at least one pressure of the flowing fluid medium. For example, the additional sensor element may also be a lambda sensor, the lambda sensor being, for example, a device for detecting at least one fraction of oxygen in the flowing fluid medium.

The moisture sensor may be accommodated in at least one housing of the sensor device. The housing may, for example, be an element of the sensor device which is configured to at least partially accommodate the moisture sensor. The housing may be the sensor housing, for example. The housing and/or the sensor housing may basically be a one-part or multi-part device which at least largely closes off the sensor device and/or the moisture sensor and/or the flow sensor and/or the temperature sensor and/or the pressure sensor and/or the lambda sensor from the outside, and/or at least largely protects against mechanical effects and/or other types of effects, for example chemical effects and/or moisture effects. In particular, the housing and/or the sensor housing may include at least one plug-in sensor; for example, the sensor device may be designed completely or partially as a plug-in sensor. The plug-in sensor may preferably be insertable into the flowing fluid medium, a replaceable or also a permanent insertion being conceivable. The plug-in sensor may, for example, protrude into a flow tube of the flowing fluid medium. The flow tube itself may be an integral part of the sensor device, but may also be provided as a separate part. The flow tube may, for example, include at least one opening into which the plug-in sensor is insertable. The plug-in sensor and/or the flow tube may in particular be made at least partially of a plastic material, for example with the aid of an injection molding process. "Accommodation," for example of the moisture sensor in the housing, may be understood to mean that, for example, the moisture sensor and/or the flow sensor and/or the temperature sensor and/or the pressure sensor may be at least partially, preferably completely, enclosed by the housing and/or the sensor housing. The application device may be at least partially enclosed by the housing.

The housing may have at least one opening. The application device may include the at least one opening in the housing. The opening may preferably be designed in such a way that at least a portion of the flowing fluid medium may pass into the housing and/or to the moisture sensor and/or to the application device. In principle, the opening may be an element of the housing that is configured to allow at least a portion of the flowing fluid medium to flow through the opening. The opening may, for example, be a circular and/or rectangular and/or polygonal and/or elliptical opening. The opening may have a design that is at least partially closed and/or closable. The diaphragm may, for example, at least partially close the opening. In this regard, "closing" may be understood to mean that at least a portion of the flowing fluid medium is not able to pass through the opening; for example, dirt particles may be hindered from passing through the opening. The diaphragm particularly preferably may at least partially enclose the moisture sensor, in particular at least partially enclose the sensor element. For example, the sensor element and/or the moisture sensor may be surrounded by at least one frame, preferably a plastic frame. The frame may, for example, be part of the housing, but may also have a design that is completely or partially separate. The frame may enclose at least one opening, whereby the diaphragm may be situated just below the opening, for example in the direction facing the moisture sensor and/or the sensor element below the opening.

For example, the guide rib structure may be fitted onto the diaphragm. The term "fitted" may be understood to mean, for example, that the guide rib structure is in direct contact with the diaphragm. For example, at least one gap may also be formed between the diaphragm and the guide rib structure. However, in principle an additional element of the sensor device may also be situated between the guide rib structure and the diaphragm. For example, the guide rib structure may also be connected to the diaphragm, for example by at least one glued and/or screwed-in and/or pressed connection.

The protective device may be situated with respect to the diaphragm in such a way that, for example, the flowing fluid medium acting on the moisture sensor preferably initially passes through the guide rib structure and, for example, subsequently through the diaphragm. For example, the protective device may be situated upstream from the diaphragm in a flow direction of the flowing fluid medium, preferably at least a portion of the flowing fluid medium. In principle, the fluid medium acting on the moisture sensor may be the entire flowing fluid medium and/or at least a portion of the flowing fluid medium.

The protective device may be configured, for example, to divert the flowing fluid medium at least once. A deflection of the flowing fluid medium may be understood to mean, for example, at least one change in the flow direction of at least a portion of the flowing fluid medium. The deflection may, for example, be a flow process and/or a diffusion process. The deflection may take place, for example, due to geometric properties of the protective device. Alternatively or additionally, the deflection may result from pressure differences produced by the protective device, for example.

The guide rib structure may include at least one guide rib. The guide rib structure may preferably include a plurality of guide ribs. In principle, a guide rib may be an element of the guide rib structure that is configured to guide at least a portion of the flowing fluid medium. A guide rib may preferably have an elongated geometry. An elongated geometry may be understood to mean, for example, a geometry having a high aspect ratio. The guide rib may be configured to guide at least a portion of the flowing fluid medium. In this regard, "guiding" may be understood to mean specifying a transport property, for example with regard to a speed and/or a direction of the flowing fluid medium, preferably of at least a portion of the flowing fluid medium. The guide rib may be designed as a wall, for example. A plurality of guide ribs may, for example, include guide ribs which may be situated in parallel and/or in alignment with one another and/or perpendicularly with respect to one another and/or at any arbitrary angle with respect to one another. The guide ribs of the plurality of guide ribs may be situated, for example, in one plane and/or in multiple planes.

For example, the guide ribs may be situated in an arrangement selected from the group composed of:

a longitudinal arrangement in which the guide ribs are situated essentially in parallel to a main flow direction of the flowing fluid medium;

a transverse arrangement in which the guide ribs are situated essentially perpendicularly with respect to a main flow direction of the flowing fluid medium;

a radial arrangement in which the guide ribs are situated radially with respect to one another;

a secantial arrangement in which the guide ribs are situated secantially with respect to a virtual circle;

a labyrinthine arrangement in which the guide ribs form a labyrinthine structure in which the labyrinthine structure may divert the flowing fluid medium, which acts on the moisture sensor, several times.

In this regard, the term "essentially parallel" may be understood to mean an orientation in which, for example, the guide ribs have an angle with respect to the main flow direction which is less than 90°, for example less than 45°, preferably less than 10°, particularly preferably 0°. The term "essentially perpendicular" may be understood to mean, for example, an arrangement in which the main flow direction forms an angle with respect to the guide ribs which is greater than 0°, for example 45° to 135°, preferably 80° to 100°, particularly preferably 90°. The term "main flow direction" may be understood to mean a flow direction of the flowing fluid medium, particularly preferably a flow direction of the largest fraction of the flowing fluid medium, for example a flow direction of the flowing fluid medium over the sensor device and/or over the application device and/or over the housing and/or over the opening. The term "radial" may be understood to mean an arrangement of the guide ribs, in particular a radial arrangement, in which the guide ribs may be oriented toward at least one shared orientation point, for example in each case essentially along a radius, for example a virtual circle. The orientation point may be a vanishing point, for example. For example, a radial arrangement may include an arrangement of the guide ribs that is similar to the arrangement of rotor blades of a fan. The guide rib structure, preferably the guide ribs, may have a stationary design, for example fixed to the housing, in particular fixed to a surface of the housing and/or to the diaphragm. However, in principle the guide ribs may also have a design that is at least partially movable, for example as an integral part of at least one fan. The terms "secantial arrangement" and/or "secantial" may be understood to mean, for example, that the guide ribs may be situated along secants of a virtual circle. The terms "labyrinthine arrangement" and/or "labyrinthine structure" may be understood to mean a system of supply lines and/or paths of the flowing fluid medium which may be formed by the guide ribs, at least a portion of the flowing fluid medium being specified by at least one, preferably multiple, changes in the flow direction, in particular by the guide ribs.

A guide rib may be designed, for example, as a lamella and/or as a blade and/or as a rotor blade and/or as a wall. The guide rib may have a cuboidal design, but may also be designed as a solid parallelepiped and/or rod and/or cylinder and/or tube. The guide rib may be rotated about at least one axis, for example an axis of the solid parallelepiped, for example in the sense of torsion and/or bending.

The protective device may have at least one cover. A cover may be understood to mean, for example, an element which is configured to at least partially cover at least a portion of the application device. For example, the cover may be a lid. The cover may in particular be a disk-shaped cover that is fitted onto the guide rib structure. For example, the guide rib structure may be reversibly or irreversibly joined to the cover, for example glued and/or pressed. The cover may, for example, be situated, as described above, essentially in parallel to a surface, in particular to a wall and/or a lid, of the housing. The guide ribs may in particular be designed as spacers between the housing and the cover. A "disk-shaped cover" may be understood in particular to mean a cover having an essentially planar, for example flat, design. However, other designs are also possible in principle.

The protective device may be configured to throttle the flow of at least a portion of the flowing fluid medium. "Throttling" of the flow may be understood to mean a reduction in the flow velocity. For this purpose, the protective device may, for example, have additional structures, for example roughness of the guide ribs and/or lamella-like structures, situated essentially perpendicularly with respect to the flow, on at least one surface of the guide rib.

The protective device may be configured, for example, to guide at least a portion of the flowing fluid medium to the moisture sensor, and optionally also to lead same away from the moisture sensor, for example after a detection of the moisture has been completed by the moisture sensor. Alternatively or additionally, the application device may be configured, for example, to guide at least a portion of the flowing fluid medium to the moisture sensor, and optionally to lead same away again from the moisture sensor. For example, the application device and/or the protective device may form at least a portion of a loop, which preferably is not completely closed, of the flowing fluid medium, preferably via the moisture sensor.

The protective device, in particular the guide rib structure, may be at least partially integrated into the housing of the sensor device, in particular into a housing cover of the housing. The housing cover may, for example, be an element of the housing that is configured to at least partially cover and/or close off the housing, for example toward the main flow of the flowing fluid medium. The housing cover may, for example, be the electronics compartment cover.

The above-described sensor device may have numerous advantages over known sensor devices. For example, a rate of particles which may reach the diaphragm, for example a moisture-permeable diaphragm, of the sensor device and/or of the application device and/or of the moisture sensor, as well as the velocity of the particles, may be reduced. The sensor device, in particular the device according to the present invention, may, for example, shield the diaphragm from the largest possible portion of the solid particles and/or water droplets and/or oil droplets present in the intake air. The cover, which in particular is designed as the cover of the opening, together with the guide rib structure, for example, may essentially in particular meet two functions:

a direct impact by particles and/or droplets of media which are liquid, for example, may be prevented in particular by the labyrinthine structure as a labyrinth-like configuration, for example. A bulk of the particles may be intercepted by flow deflection, for example, preferably before they are able to reach the diaphragm, which preferably may be situated above a sensor element, in particular the moisture sensor;

particle-free air, in particular a particle-free flowing fluid medium, for example a flowing fluid medium from which particles have been removed, may be led to the sensor element and optionally in addition once again supplied to the main flow. A sufficient air exchange, in particular an exchange of the flowing fluid medium, may thus be ensured, for example to improve a response characteristic of the sensor device, for example the sensor. One advantage of the sensor device according to the present invention, designed as a unit, for example, may be that when the motor, for example the motor of the internal combustion engine, is stopped, the sensor device is suitable for effectively keeping oil mist exiting from a crankcase away from the diaphragm, and thus, for example, preferably preventing or at least reducing a planar covering of the diaphragm with an oil film.

DETAILED DESCRIPTION OF THE INVENTION

Figure 1A:
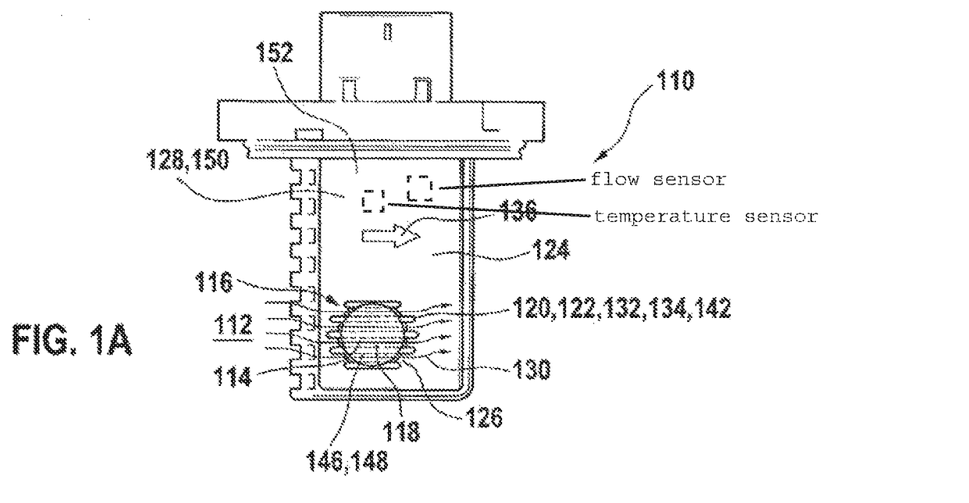
FIG. 1A shows a first exemplary embodiment of a sensor device according to the present invention for detecting at least one property of a flowing fluid medium.
Figure 2:
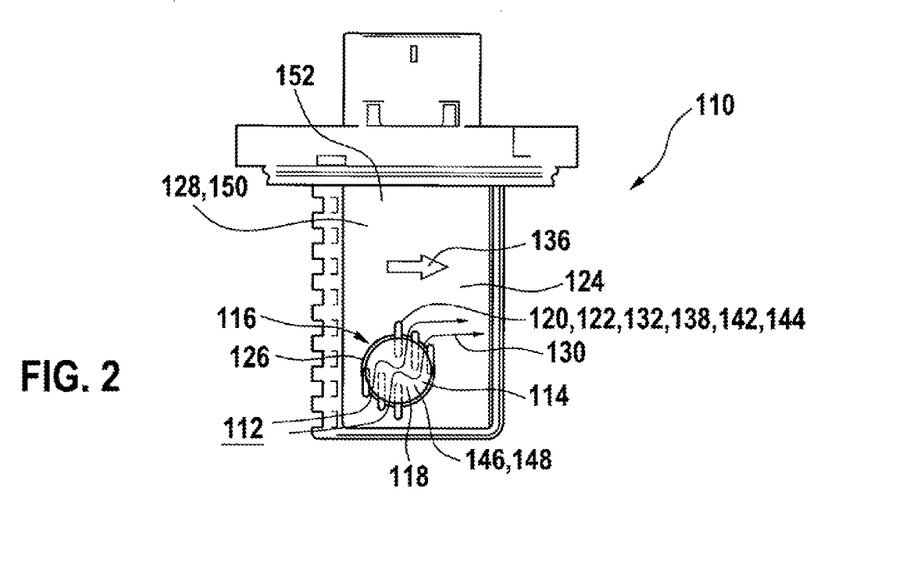
FIG. 2 shows a second exemplary embodiment of a sensor device according to the present invention for detecting at least one property of a flowing fluid medium.
Figure 3:
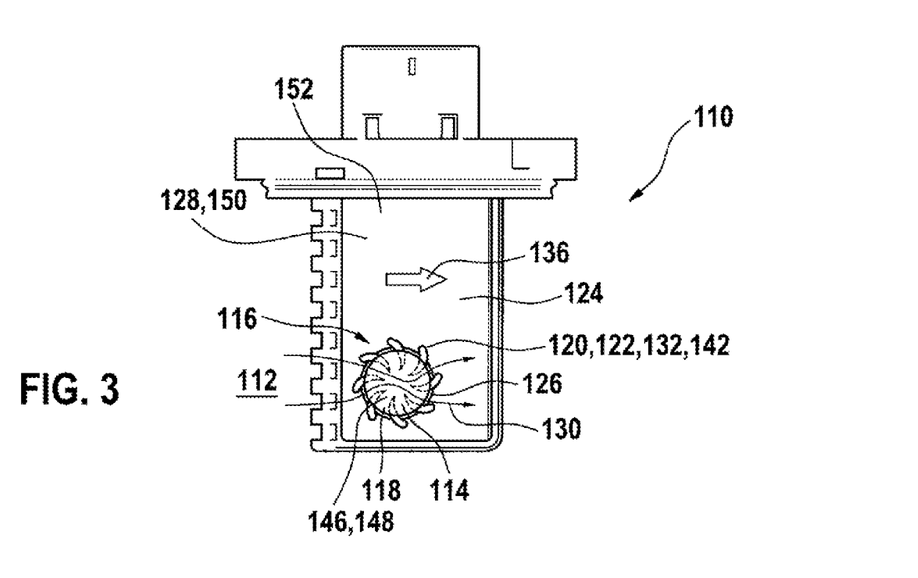
FIG. 3 shows a third exemplary embodiment of a sensor device according to the present invention for detecting at least one property of a flowing fluid medium.

FIGS. 1A, 2, and 3 illustrate in particular three exemplary embodiments of a sensor device 110 according to the present invention for detecting at least one property of a flowing fluid medium 112. The property may preferably be at least a moisture, in particular at least a humidity, and/or at least a mass flow and/or at least a temperature of flowing fluid medium 112. Sensor device 110 includes at least one moisture sensor 114. Sensor device 110 includes at least one application device 116 for applying flowing fluid medium 112 to moisture sensor 114. Application device 116 includes at least one diaphragm 118 which in particular is at least partially permeable to moisture. Application device 116 also includes at least one protective device 120. Protective device 120 has at least one guide rib structure 122.

Sensor device 110 may also include at least one flow sensor, which is not illustrated in the figures. Sensor device 110 may also include at least one temperature sensor, which is likewise not illustrated in the figures. Sensor device 110 according to the present invention may be designed as a cylinder housing variant, for example. For example, sensor device 110 according to the present invention may also be designed as a plug-in sensor. Sensor device 110 according to the present invention may represent an independent moisture sensor 114, optionally together with the temperature sensor.

Moisture sensor 114 may be accommodated in at least one housing 124 of sensor device 110. Application device 116 may include at least one opening 126 in housing 124. Diaphragm 118 may at least partially close opening 126. Diaphragm 118 may particularly preferably at least partially enclose moisture sensor 114, and in particular may at least partially enclose the sensor element. Guide rib structure 122 may be fitted onto diaphragm 118.

Protective device 120 may be situated with respect to diaphragm 118 in such a way that flowing fluid medium 112 acting on moisture sensor 114 may initially pass through guide rib structure 122, and may optionally subsequently pass through diaphragm 118. Housing 124 may be an electronics compartment cover 128, for example. Housing 124 may particularly preferably include electronics compartment cover 128, for example as a closure of housing 124. For example, as illustrated in particular in FIGS. 1B and 1C, protective device 120 may be mounted above the opening 126. Protective device 120 and/or diaphragm 118 may have separate designs, but may also be part of housing 124, in particular of electronics compartment cover 128. In particular, electronics compartment cover 128 may have the at least one opening 126. Opening 126 may be at least partially covered by guide rib structure 122.

Protective device 120 may be configured to deflect flowing fluid medium 112 at least once. This is indicated, for example, by thin arrows 130 in FIGS. 1A, 2, 3. Thin arrows 130, as illustrated in FIGS. 1A, 2, 3, in particular are not straight, but instead have deviations from a linear line layout which may show at least one deflection of flowing fluid medium 112, in particular by protective device 120 and/or by guide rib structure 122. Protective device 120, for example, which is designed in particular as a flow device, is preferably fitted onto the diaphragm, which is unprotected in devices from the related art, in sensor device 110 according to the present invention. Protective device 120, in particular the flow device, may in particular ensure one or multiple deflection(s) and/or throttling(s) of the air flow, in particular of flowing fluid medium 112.

Figure 1B:
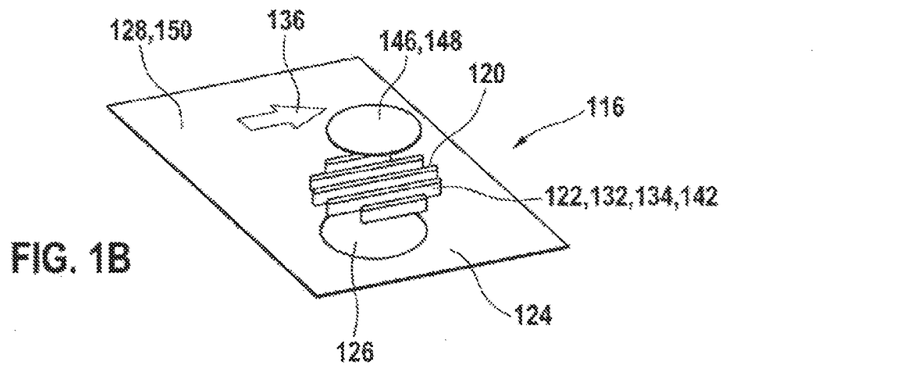
FIG. 1B shows an exploded drawing of the protective device of the first exemplary embodiment of the sensor device according to the present invention.
Figure 1C:
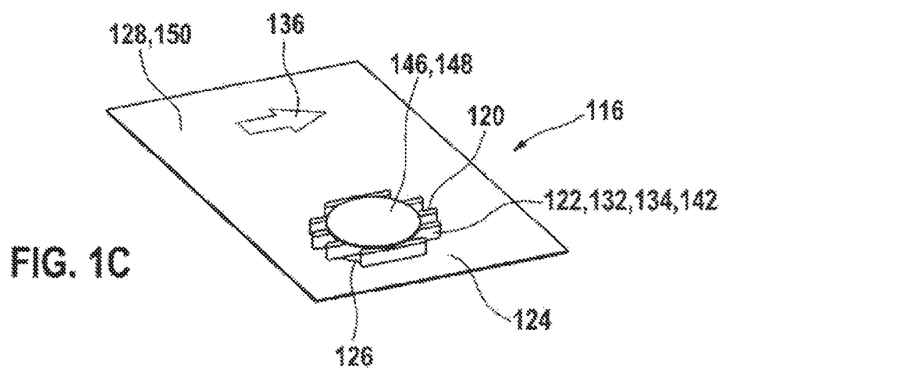
FIG. 1C shows a schematic illustration of the protective device of the first exemplary embodiment of the sensor device according to the present invention.

Guide rib structure 122 may include a guide rib 132, preferably a plurality of guide ribs 132. Guide ribs 132 may be situated in an arrangement selected from the group composed of:
- a longitudinal arrangement 134 as described in the first exemplary embodiment, for example, as illustrated in FIGS. 1A, 1B, and 1C, in which guide ribs 132 may be situated essentially in parallel to a main flow direction 136 of flowing fluid medium 112;
- a transverse arrangement 138 as described in the second exemplary embodiment, for example, as illustrated in FIG. 2, for example, in which guide ribs 132 may be situated essentially perpendicularly with respect to a main flow direction 136 of flowing fluid medium 112;
- a radial arrangement 140 as described in the third exemplary embodiment, for example, as illustrated in FIG. 3, in which guide ribs 132 are situated radially with respect to one another;
- a secantial arrangement 142 as described, for example, in the first and second exemplary embodiments as illustrated in FIGS. 1A, 1B, 1C, and 2, in which guide ribs 132 may be situated secantially with respect to a virtual circle;
- a labyrinthine arrangement 144 as described, for example, in the second exemplary embodiment as illustrated in FIG. 2, in which guide ribs 132 may form a labyrinthine structure in which the labyrinthine structure may divert flowing fluid medium 112, acting on moisture sensor 114, several times.

The virtual circle may, for example, also be real, for example as circular opening 126 in housing 124. In principle, opening 126 may also have a different shape; for example, opening 126 may have at least one corner; for example, opening 126 may be rectangular and/or polygonal and/or elliptical. Guide ribs 132 may extend from one edge of opening 126 to another edge of opening 126, but may also protrude into opening 126 only from one edge of opening 126, for example without reaching another edge of opening 126. For example, guide ribs 132 may also be situated only outside opening 126. The illustrated exemplary embodiments in FIGS. 1A, 2, and 3 differ in particular by different arrangements of guide ribs 132 and/or by different guide rib structures 122. Thin arrows 130 schematically denote a flow through guide ribs 132 and/or through guide rib structure 122. In FIG. 1A, guide ribs 132 are situated essentially in main flow direction 136 with the lowest degree of deflection. In the second exemplary embodiment according to FIG. 2, guide ribs 132 are situated essentially transversely with respect to main flow direction 136. In the third exemplary embodiment as illustrated in FIG. 3, guide rib structure 122 has, for example, lamellae which are circumferentially inclined at an angle.

Protective device 120 may have at least one cover 146. Cover 146 is illustrated as transparent in FIGS. 1A, 2, and 3. In principle, cover 146 may have a transparent, untransparent, or opaque design. Cover 146 and/or guide rib structure 122 and/or housing 124 and/or application device 116 may be made completely or partially of a plastic. Cover 146 may in particular be a cover 146, for example a disk-shaped cover 148, in particular a circular cover 146, which is fitted onto a guide rib structure 122 and/or onto guide ribs 132. In principle, cover 146 may also have a different design. For example, cover 146 may have at least one corner. For example, cover 146 may be at least partially circular. Cover 146 may be designed, for example, as a polygon and/or as an ellipse. For example, cover 146 may have a separate design, or may form an element together with guide rib structure 122.

Protective device 120 may be configured to throttle a flow of at least a portion of flowing fluid medium 112. Protective device 120 may in particular be designed in such a way that at least a velocity of large solid particles, which, for example, could cause mechanical damage to diaphragm 118, may be reduced, preferably before the large solid particles are able to strike diaphragm 118. Protective device 120 may be configured to guide at least a portion of flowing fluid medium 112 to moisture sensor 114, and also optionally to lead same away from moisture sensor 114. For example, flowing fluid medium 112, for example, an air flow, may be guided over guide rib structure 122 to moisture sensor 114, in particular to the sensor element and/or to another sensor element, and optionally led back to main flow direction 136, for example to the main flow. Flowing fluid medium 112, for example the flow, may reach diaphragm 118 in such a way that a preferably unhindered gas exchange, for example of water vapor and/or of flowing fluid medium 112, may be ensured, and/or a deposition of liquid and/or solids on diaphragm 118 may be reduced.

Protective device 120, in particular guide rib structure 122, may be at least partially integrated into housing 124 of sensor device 110, in particular into or onto a housing cover 150 of housing 124, for example integrated into electronics compartment cover 128. FIGS. 1B and 1C schematically illustrate the design of housing cover 150, in particular of electronics compartment cover 128, in particular having a partial cover 146 of opening 126, for example above moisture sensor 114, in particular above the sensor element and/or above an additional sensor element. In particular guide rib structure 122, for example as the structure composed of guide ribs 132, which preferably may be closed at the top, for example by cover 146, may be situated above opening 126 in electronics compartment cover 128. Flowing fluid medium 112, for example air, may pass through between guide ribs 132 and reach moisture sensor 114 and/or a sensor element, for example moisture sensor 114 and/or the flow sensor and/or the temperature sensor and/or a pressure sensor and/or another sensor. At least one electronic module 152 may be accommodated in housing 124. Electronic module 152 may include, for example, the flow sensor and/or the temperature sensor and/or the pressure sensor and/or moisture sensor 114. Electronic module 152 may be at least partially situated in at least one electronics compartment of housing 124. The electronics compartment may be understood to mean, for example, a partially or completely closed space within housing 124 which may be closed off by housing 124 in at least one direction. The electronics compartment may preferably have at least one depression in housing 124, for example a cuboidal depression, which is accessible from a surface of housing 124. The electronics compartment may be accessible, for example, from the surface, for example through electronics compartment cover 128 or through another closure element, for assembly. The electronics compartment may be permanently or reversibly closable by electronics compartment cover 128. Electronic module 152 may in particular include, for example support, at least one control circuit and/or evaluation circuit, whereby the control circuit and/or evaluation circuit may be configured to control moisture sensor 114 and/or the flow sensor and/or the temperature sensor and/or the pressure sensor or some other sensor or some other sensor element and/or to receive signals of the mentioned sensors, preferably of moisture sensor 114. Accordingly, electronic module 152 may have at least one circuit carrier, for example. In addition, electronic module 152 may in particular have at least one sensor support which may preferably be mechanically connected to the circuit carrier. For example, the circuit carrier may be situated in the electronics compartment of housing 124. For example, the sensor support may protrude from the electronics compartment into flowing fluid medium 112. The sensor support may include, for example, moisture sensor 114 and/or a sensor for the flow sensor and/or the temperature sensor and/or the pressure sensor and/or some other sensor and/or some other sensor element. It is particularly preferred for housing 124 to have at least one channel through which flowing fluid medium 112 may flow. The channel through which the flow may pass may, for example, be part of application device 116, but may also have a separate design. The sensor support of electronic module 152, which may support moisture sensor 114 and/or the flow sensor, for example, may protrude from the electronics compartment into the at least one channel in housing 124 through which flowing fluid medium 112 may flow. This at least one channel may in particular have a one-part design, but may also have at least one main channel and at least one bypass channel which branches off from this main channel, whereby the sensor support and/or moisture sensor 114 and/or the flow sensor and/or the temperature sensor and/or the pressure sensor may preferably protrude into the bypass channel. The circuit carrier of electronic module 152 may in particular include at least one printed circuit board which may be used alone, for example, or which may also be mounted on a mechanical carrier; for example, the carrier may be made, at least partially, of at least one metallic material. The sensor support may be directly connected to the circuit carrier, or also to the carrier. Other designs are also possible. Thus, for example, it is conceivable for electronic module 152 to be made from a printed circuit board material, it being possible for the circuit carrier as well as the sensor support to be made from the printed circuit board material, preferably from at least one piece of the printed circuit board material. Alternatively or additionally, it may also be possible to use injection-molded printed circuit boards known from the related art as electronic module 152, for example injection-molded printed circuit boards. Various designs are conceivable. Electronic module 152 and/or the evaluation and/or control device may include at least one controller and/or at least one computer and/or at least one data processing device.

What is claimed is:

1. A sensor device for detecting at least one property of a flowing medium, comprising:
    at least one moisture sensor; and
        at least one application device for applying the flowing fluid medium to the moisture sensor, wherein the application device includes at least one diaphragm and at least one protective device which has at least one guide rib structure;
        wherein the guide rib structure includes multiple guide ribs which are arranged in one of:
        a longitudinal arrangement in which the guide ribs are situated essentially in parallel to a main flow direction of the flowing fluid medium;
        a transverse arrangement in which the guide ribs are situated essentially perpendicularly with respect to a main flow direction of the flowing fluid medium;
        a radial arrangement in which the guide ribs are situated radially with respect to one another;
        a secantial arrangement in which the guide ribs are situated secantially with respect to a virtual circle; and
        a labyrinthine arrangement in which the guide ribs form a labyrinthine structure in which the labyrinthine structure diverts the flowing fluid medium, which acts on the moisture sensor, multiple several times.

2. The sensor device as recited in claim 1, further comprising:
    at least one flow sensor.

3. The sensor device as recited in claim 1, further comprising:
    at least one temperature sensor.

4. The sensor device as recited in claim 1, wherein:
    the moisture sensor is accommodated in at least one housing of the sensor device;
    the at least one application device includes at least one opening in the housing; and
    the diaphragm at least partially encloses the moisture sensor.

5. The sensor device as recited in claim 1, wherein the at least one protective device is situated with respect to the diaphragm in such a way that the flowing fluid medium acting on the moisture sensor initially passes through the guide rib structure and subsequently through the diaphragm.

6. The sensor device as recited in claim 1, wherein the at least one protective device has at least one cover fitted onto the guide rib structure.

7. The sensor device as recited in claim 1, wherein the at least one protective device is configured to throttle a flow of at least a portion of the flowing fluid medium.

8. The sensor device as recited in claim 1, wherein the at least one protective device is configured to guide at least a portion of the flowing fluid medium to the moisture sensor and away from the moisture sensor.

9. The sensor device as recited in claim 1, wherein the protective device is at least partially integrated into a housing cover of the housing.

* * * * *